United States Patent
Dumas et al.

(10) Patent No.: US 12,138,337 B2
(45) Date of Patent: Nov. 12, 2024

(54) **COSMETIC COMPOSITION COMPRISING AN EXTRACT OF *CAESALPINIA SPINOSA*, AN EXTRACT OF *KAPPAPHYCUS ALVAREZII*, AND A *THEOBROMA CACAO* L BEAN HYDROLYSATE**

(71) Applicant: L V M H RECHERCHE, Saint Jean de Braye (FR)

(72) Inventors: Marc Dumas, Saint Jean le Blanc (FR); David Notte, Orleans (FR); Françoise Pellicier, Loury (FR)

(73) Assignee: L V M H Recherche, Saint Jean de Braye (FR)

( * ) Notice: Subject to any disclaimer, the term of this patent is extended or adjusted under 35 U.S.C. 154(b) by 1148 days.

(21) Appl. No.: 16/956,060

(22) PCT Filed: Dec. 21, 2018

(86) PCT No.: PCT/FR2018/053503
§ 371 (c)(1),
(2) Date: Jun. 19, 2020

(87) PCT Pub. No.: WO2019/122777
PCT Pub. Date: Jun. 27, 2019

(65) Prior Publication Data
US 2023/0210751 A1    Jul. 6, 2023

(30) Foreign Application Priority Data
Dec. 22, 2017  (FR) ........................ 1763141

(51) Int. Cl.
| | | |
|---|---|---|
| *A61K 36/00* | (2006.01) | |
| *A61K 8/73* | (2006.01) | |
| *A61K 8/9789* | (2017.01) | |
| *A61Q 1/02* | (2006.01) | |
| *A61Q 1/04* | (2006.01) | |
| *A61Q 1/10* | (2006.01) | |
| *A61Q 17/00* | (2006.01) | |
| *A61Q 19/08* | (2006.01) | |

(52) U.S. Cl.
CPC ............ *A61K 8/737* (2013.01); *A61K 8/9789* (2017.08); *A61Q 1/02* (2013.01); *A61Q 1/04* (2013.01); *A61Q 1/10* (2013.01); *A61Q 17/005* (2013.01); *A61Q 19/08* (2013.01)

(58) Field of Classification Search
CPC .................................................. A61K 31/736
See application file for complete search history.

(56) References Cited

U.S. PATENT DOCUMENTS

| | | | |
|---|---|---|---|
| 2017/0049692 A1 | 2/2017 | Stout et al. | |
| 2019/0038543 A1* | 2/2019 | Paufique | ............... A61K 36/48 |
| 2019/0075813 A1* | 3/2019 | Coquet | ............... A23L 33/105 |

FOREIGN PATENT DOCUMENTS

| | | | | |
|---|---|---|---|---|
| CN | 1809593 A | 7/2006 | | |
| CN | 107397714 A | 11/2017 | | |
| FR | 3047172 A1 * | 8/2017 | ............. | A61K 36/04 |
| WO | WO 2016/142767 A1 | 9/2016 | | |
| WO | 2017019792 A1 | 2/2017 | | |
| WO | 2017129780 A1 | 8/2017 | | |
| WO | WO-2017157998 A1 * | 9/2017 | ............... | A23G 1/30 |
| WO | WO 2017/173244 A1 | 10/2017 | | |

OTHER PUBLICATIONS

Alekseyenko et al., Community differentiation of the cutaneous microbiota in psoriasis, 1(31) Microbiome 1-17 (2013).
Flores et al., Microbiome of Affected and Unaffected Skin of Patients with Atopic Dermatitis Before and After Emollient Treatment, 13(11) Journal of Drugs in Dermatology 611-618 (Nov. 2014).
Nys et al., Skin mild hypoxia enhances kiling of UVB-damaged keratinocytes through reactive oxygen species-mediated apoptosis requiring Noxa and Bim 52(6) 1111-1120 (Mar. 2012) (Abstract Only).
Staudinger et al., Molecular analysis of the prevalent microbiota of human male and female forehead skin compared to forearm skin and the influence of make-up, 110 Journal of Applied Microbiology 1381-1389 (2011).
Straseski et al., Oxygen deprivation inhibits basal keratinocyte proliferation in a model of human skin and induces regio-specific changes in the distribution of epidermal adherens junction proteins, aquaporin-3, and glycogen, 17(4) Wound Repair Regen. 606-616 (2009).
Xia et al., Differential Activation of Migration by Hypoxia in Keratinocytes Isolated from Donors of Increasing Age: Implication for Chronic Wounds in the Elderly, 116(1) The Journal of Investigative Dermatology 50-56 (Jan. 2001).
Chinese Office Action in corresponding Chinese Patent Application No. 2022071502257620 with English translation (mailed on Jul. 20, 2022).
Japanese Office Action in corresponding Japanese Patent Application No. 2020-534847 with English translation (mailed on Jan. 10, 2023).

* cited by examiner

*Primary Examiner* — Qiuwen Mi

(74) *Attorney, Agent, or Firm* — Panitch Schwarze Belisario & Nadel LLP; Erin M. Dunston

(57) ABSTRACT

A cosmetic composition comprising, in a physiologically acceptable medium, at least: (1) a cosmetic agent consisting of galactomannans with molar masses of 5 kDa to 630 kDa, preferably between 5 and 120 kDa, more preferably between 8 and 80 kDa, and cross-linked sulfated galactans with molar masses of 7 kDa and 3000 kDa, preferably between 7 and 1100 kDa, more preferably between 8 and 200 kDa, and (2) a *Theobroma cacao* L bean hydrolysate, and its use in particular for maintaining the balance of the skin microbiota and promoting and/or improving the wear of make-up.

9 Claims, No Drawings

COSMETIC COMPOSITION COMPRISING AN EXTRACT OF *CAESALPINIA SPINOSA*, AN EXTRACT OF *KAPPAPHYCUS ALVAREZII*, AND A *THEOBROMA CACAO* L BEAN HYDROLYSATE

CROSS-REFERENCE TO RELATED APPLICATIONS

This application is a U.S. National Stage Application pursuant to 35 U.S.C. § 371 of International Patent Application PCT/FR2018/053503, filed on Dec. 21, 2018, and published as WO 2019/122777 on Jun. 27, 2019, which claims priority to French Patent Application 1763141, filed on Dec. 22, 2017, all of which are incorporated herein by reference in their entireties for all purposes.

FIELD OF THE INVENTION

The present invention relates to a cosmetic composition comprising a cosmetic agent consisting of galactomannans and cross-linked sulfated galactans, and a *Theobroma cacao* L bean hydrolysate, and its use in particular for maintaining the balance of the skin microbiota and promoting and/or improving the wear of make-up.

RELATED ART

The skin, the largest human organ, is colonized by billions of microorganisms (bacteria, yeasts, fungi, viruses, etc.) collectively known as 'microbiota' or 'microflora'. The term 'skin microbiome' refers to all these microorganisms, their genome and their interactions with their environment.

The number of bacteria present on the skin can reach millions per $cm^2$.

The human skin flora can be subdivided into two groups:
Transient flora composed of mostly harmless fungi, viruses and bacteria, called saprophytes, which feed on decaying organic matter from the environment. This flora is not permanent; it varies during the day, depending on the activities carried out and variations in the surrounding conditions and the exposure of individuals to these conditions. The most common transient species are *Staphylococcus aureus, Escherichia coli, Pseudomonas aeruginosa* and species of *Bacillus;*
The resident flora is made up of commensal germs, i.e. living thanks to their host without causing it any damage. The composition of this flora is fixed, and after disturbance, its same components spontaneously reform. These microorganisms (Gram-positive, Gram-negative bacteria, etc.) inhabit the epidermis and are mainly found in the upper layers of the stratum *corneum* as well as in the ducts of the sweat glands and pilosebaceous follicles and the epidermal appendages that are the nails and hair.

These microorganisms are essential to life. Beyond their role in the development of body odor, they are closely linked to the maintenance of healthy skin. Resident and transient microbes do not cause disease or dysfunction under normal conditions, i.e. when hygiene is adequate and when the resident flora, immune responses and barrier function of the skin are intact. The skin microbiota is thus able to act as a barrier and protect its host.

At the same time, the epidermis generates antimicrobial lipids and peptides, such as β-defensins, receptors dedicated to the recognition of pathogens, which together form 'innate skin immunity'.

As they grow and multiply, resident bacteria also produce toxic metabolites, bacteriocins, and serine proteases such as those of *Staphylococcus epidermidis*, which inhibit the growth of other microorganisms and prevent the formation of their biofilm by which they adhere to the skin.

The commensal flora stimulates the skin barrier and innate immunity, thus maintaining a healthy and resistant skin. The balance of the skin's microbiota, as well as the expression of the ecological conditions of the skin environment (temperature, pH, salinity, hormone levels, lipid and protein content, water and oxygen content, UV exposure) are also essential for this maintenance.

In addition to intrinsic factors such as age, gender, genetic make-up and immune reactivity, extrinsic factors such as climate (temperature, ambient humidity, UV), drug treatments, the use of hygiene, care or make-up cosmetic products can have a significant impact on the composition of skin microbial communities.

It has also been shown that the composition of the skin microbiota is influenced by the ability of the skin to retain the water it contains and the production of sebum. Sebum level is negatively correlated with the 3 diversity indices from 16S taxonomic data (order, family, genus and species) and the same trend was observed for insensible water loss (reflecting the quality of the skin barrier).

These studies, presented at the ASCB Annual Meeting in San Francisco in December 2016 by C Heuséle et al. and titled 'Microbiota diversity on healthy women's face in relation to skin biophysical characteristics', show a correlation between sebum production and skin barrier function with the composition and diversity of the microbiota.

The variability of the human skin microbiota can then lead to an alteration of its structure (dysbiosis) and have consequences on health by causing the occurrence of skin dysfunctions or contribute to the development of pathologies via the colonization and proliferation of the resident and/or transient flora. For example, a decrease in microbial diversity is observed in certain pathologies such as atopic dermatitis (Flores G et al. J Drugs Dermatol 2014: 13(11): 1365-72) and psoriasis (Alekseyenko A et al., Microbiome 2013: 1(131): 2-17).

The application in particular of make-up compositions, such as foundations, can thus disturb the balance of the skin microbiota, in particular by disturbing the bacterial diversity. The invisible film of make-up applied to the skin can also transiently generate a modification of the skin's hydrolipidic balance and desquamation, factors likely to deregulate the balance of the skin microbiota.

The invisible film of make-up applied to the skin can also temporarily generate a hypoxic condition that can alter the skin microbiota, particularly the aerobic microorganisms that live on the surface of the integument where the oxygen content is highest. Indeed, it has been shown that an application of foundation has a significant impact on bacterial diversity (Staudinger T et al. J Appl. Microbiol 2011: 110 (6): 1381-9.

The lipid film formed by excessive sebum production can also temporarily generate a hypoxic condition that can modify the skin microbiota, in particular the aerobic microorganisms that live on the surface of the integument where the oxygen content is highest.

But hypoxia is also capable of altering the skin tissue itself on several levels:
by reducing the formation of desmoglein-1, a protein that forms the building blocks of cell cohesion and thus epidermal resistance (Straseski J et al. Wound Repair Regen. 2009; 17(4): 606-616), by also reducing the formation of aquaporin 3, a protein that transports water to the epidermis to hydrate the skin (Straseski J et al. Wound Repair Regen. 2009; 17(4): 606-616), by stimulating the production of reactive oxygen species (ROS) that alter skin constituents and cells (Nys K et al. Free Radic Biol Med. 2012; 52(6):1111-20)

by inhibiting the formation of differentiation keratins such as keratin 10 (Straseski J et al. Wound Repair Regen. 2009; 17(4): 606-616), and/or by increasing the presence of matrix metalloproteinases or MMPs (Xia Y P et al. J. Invest. Dermatol. 2001; 116: 50-56) which break down skin constituents such as collagen which can impact skin density and firmness and consequently the opening of pores and the formation of fine lines and wrinkles.

It is therefore understandable why it is advantageous, in particular for make-up compositions for keratin materials and in particular for the skin, or compositions for oily skin or skin with an oily tendency, to have ingredients that are able to protect the skin ecosystem from the consequences of hypoxia by ensuring at least one of the following protective actions:

by preserving the microbiota and its diversity by providing the skin conditions that allow it, such as strengthening the skin barrier and controlling sebum production, by enhancing the cohesion of the epidermis to strengthen the skin's resistance, by stimulating the formation of the skin barrier to maintain sufficient moisture in the skin, by detoxifying the skin of reactive oxygen species, by inhibiting the formation of MMPs, and/or by stimulating the formation of the hypoxia inducing factor or HIF which protects skin cells from hypoxia.

There thus remains a need to develop new cosmetic make-up compositions for keratin materials, in particular for the skin, capable in particular of preserving the diversity of the microbiota, controlling its development and improving the quality of keratin materials (skin, mucous membranes, hair and nails) and in particular the skin, the relief and the grain of its surface which constitutes an ecological niche for these microorganisms, in particular to maintain the skin ecosystem and/or maintain the balance of the skin microbiota, in particular microbial diversity, to strengthen the skin barrier, to improve the skin's resistance to stress, in particular to prevent and/or limit the cutaneous consequences of a hypoxic environment, to reduce cutaneous inflammation, to promote desquamation and/or epidermal renewal, to reduce the loss of firmness involved in the relaxation of pores and the formation of wrinkles and fine lines, to improve the homogeneity of the complexion, and/or to promote and/or improve the wear of make-up and the homogeneity of its distribution on the surface of the skin.

The Applicant demonstrated that the combination of a cosmetic agent consisting of galactomannans and cross-linked sulfated galactans, and a *Theobroma cacao* L bean hydrolysate, met this need. In particular, the Applicant was able to show that a composition comprising a cosmetic agent consisting of galactomannans obtained from *Caesalpinia spinosa* with molar masses of between 1 and 150 kDa and cross-linked sulfated galactans obtained from *Kappaphycus alvarezii* with molar masses of between 1 and 150 kDa, and a *Theobroma cacao* L bean hydrolysate, prevented and/or diminished the effects of stress on keratinocytes, promoted cell renewal, thus improving the skin barrier function and maintaining the balance of the skin microbiota.

DISCLOSURE OF THE INVENTION

The invention therefore relates in particular to a cosmetic composition comprising, in a physiologically acceptable medium, at least:

a) a cosmetic agent consisting of galactomannans with molar masses comprised between 5 and 630 kDa, preferably between 5 and 120 kDa, more preferably between 8 and 80 kDa, and cross-linked sulfated galactans with molar masses comprised between 7 and 3000 kDa, preferably between 7 and 1100 kDa, more preferably between 8 and 200 kDa, and b) a *Theobroma cacao* L bean hydrolysate.

Another subject matter of the invention relates to a cosmetic process for the care and/or make-up of keratin materials, in particular the skin, the lips and/or the eyes, comprising at least the application to said keratin materials, in particular the skin of the face, of a composition according to the invention.

The invention also relates to the non-therapeutic cosmetic use of at least one cosmetic agent consisting of galactomannans with molar masses comprised between 5 and 630 kDa and cross-linked sulfated galactans with molar masses comprised between 7 and 3000 kDa, and of at least one *Theobroma cacao* L. bean hydrolysate as defined according to the invention as a combination for maintaining the skin ecosystem and/or maintaining the balance of the skin microbiota, in particular the microbial diversity, strengthening the skin barrier and its hydrolipidic film, improving the integrity and the resistance of the skin to stress, in particular preventing and/or limiting the cutaneous consequences of a hypoxic environment, promoting desquamation and/or epidermal renewal, reducing loss of firmness, reducing relaxation of pores, reducing surface irregularities, improving the homogeneity of the complexion, and/or promoting and/or improving the wear of make-up and the homogeneity of the deposit.

Another subject matter of the invention relates to at least one cosmetic agent consisting of galactomannans with molar masses comprised between 5 and 630 kDa and cross-linked sulfated galactans with molar masses comprised between 7 and 3000 kDa, and at least one *Theobroma cacao* L. bean hydrolysate as defined according to the invention or of a composition containing same, for use in treating and/or reducing disorders associated with hyperseborrhea, in particular sebum-dependent inflammation and/or bacterial proliferation, in particular in subjects with oily skin or skin with an oily tendency.

Definitions

According to the invention, 'keratin materials' means the skin, the mucous membranes (especially the lips), and the hair and nails. According to a particular embodiment, the composition is intended for topical application to the skin, the lips or the hair and nails, preferably the skin.

'Skin' means in particular the skin of the face and/or neck, in particular the skin of the face, including the more specific areas of the eyelids (falling within the category of eye make-up products) and the eye contour area.

'Skin microbiota' or 'microflora' means the microorganisms (bacteria, yeasts, fungi, viruses, etc.) present on the surface of keratin materials and in particular the skin.

The term 'skin microbiome' refers to all these microorganisms, their genome and their interactions with their environment.

According to the invention, 'skin ecosystem', otherwise known as 'skin biosphere', refers to the skin microbiota and its host, the skin. 'Imbalance of the skin microbiota' means in particular an imbalance in the composition and/or the diversity of the skin microbiota.

According to the invention, 'maintaining the skin ecosystem and/or maintaining the balance of the skin microbiota, in particular microbial diversity' means the capacity of the active ingredients or of a composition containing same to preserve or maintain the natural balance of the skin ecosystem, including under conditions of disturbance linked to internal and/or external factors. 'Maintaining the balance of the skin microbiota' means in particular preserving or maintaining the composition and/or diversity of the microbiota and controlling its development.

'Homogeneity of the complexion' means in particular a luminous, homogeneous complexion, also called 'radiance of the complexion', as opposed to 'alteration of the complexion' which designates in particular a dull, inhomogeneous, blurred complexion, presenting irregularities of surface and/or color. In the case of oily skin, the alteration of complexion includes in particular a shiny complexion and a perception of discomfort and manifestations felt as skin imperfections or aesthetic disorders.

According to the invention, 'surface irregularities', otherwise called 'skin imperfections', means in particular irregularities in relief (e.g. pores, scales, wrinkles and fine lines, imperfect skin texture) and/or irregularities in color. For the lips, these irregularities in relief may include chapped or cracked lips.

According to the invention, 'preventing and/or limiting the cutaneous consequences of a hypoxic environment' means in particular maintaining the diversity of the microbiota, and/or preventing and/or improving skin alterations linked to a transitory hypoxic condition, such as a decrease in cell cohesion, a decrease in the water supply to the epidermis, an increase in the production of reactive oxygen molecules, an inhibition of the formation of differentiation keratins and/or an increase in the degradation of collagen.

'Oily skin or skin with an oily tendency' is understood to be oily skin characterized by an excessive presence of sebum on its surface, the product of secretion of the sebaceous glands. This production of sebum is ensured more particularly by the sebocytes through a process of cellular differentiation and synthesis or accumulation of lipids called lipogenesis. It is also known as hyperseborrheic skin.

Oily skin is often associated with a desquamation defect, an inflammatory terrain and/or lipid oxidation, which can cause a shiny complexion, imperfect skin texture, a perception of discomfort and perceived manifestations such as skin imperfections or aesthetic disorders; such skin also presents a poorer wear of make-up during the day and particularly in the afternoon when sebaceous production is at its peak.

In addition to its unsightly appearance, oily skin can be a breeding ground for the proliferation of microorganisms and thus contribute to the occurrence of skin disorders (e.g. acne lesions).

This is known as oily or hyperseborrheic skin with an acneic tendency.

'Aesthetic skin disorders or non-pathological disorders associated with oily skin or skin with an oily tendency' are understood to be disorders due to hyperseborrhea, a desquamation defect, a hypoxic environment and/or an imbalance of the microbiota. In particular, the associated aesthetic skin disorders are non-pathological disorders selected from skin exhibiting an imbalance of the skin microbiota, a desquamation defect, an oxidation of lipids, an alteration of the complexion, in particular a shiny complexion, a perception of discomfort, surface irregularities, in particular follicular orifices or dilated pores, an imperfect skin texture, and/or skin exhibiting a less good make-up wear.

DETAILED DESCRIPTION OF THE INVENTION

A first subject matter of the invention is therefore a cosmetic composition comprising, in a physiologically acceptable medium, at least:
 a) a cosmetic agent consisting of galactomannans with molar masses comprised between and 630 kDa, preferably between 5 and 120 kDa, more preferably between 8 and 80 kDa, and cross-linked sulfated galactans with molar masses comprised between 7 and 3000 kDa, preferably between 7 and 1100 kDa, more preferably between 8 and 200 kDa, and
 (b) a *Theobroma cacao* L bean hydrolysate.

Galactomannans and Cross-Linked Sulfated Galactans

The cosmetic agent in the sense of the invention consists of biopolymers, i.e. polymers derived from plant materials, which are obtained by chemical synthesis.

These biopolymers have a film-forming effect, i.e. an effect that can create a film on the surface of the skin that is not perceptible to the naked eye, in order to protect the skin from external insult such as pollution and allergens.

Such biopolymers are described in particular in patent applications WO2017/19792 and WO2017/129780 of Société Industrielle Limousine d'Application Biologique.

The cosmetic or dermocosmetic agent used according to the invention consists of:
 galactomannans with molar masses comprised between 5 and 630 kDa, and
 cross-linked sulfated galactans with molar masses comprised between 7 and 3000 kDa.

The 'average molecular weight' of a mixture of molecules means the average molecular weight of each molecule in the mixture.

For the purposes of the invention, 'cross-linked' means a biopolymer in which a three-dimensional network has been formed by means of the formation of chemical or physical bonds between the molecules of the biopolymer.

Preferentially, the cosmetic or dermocosmetic agent consists of:
 galactomannans with an average molar mass comprised between 5 and 120 kDa, and cross-linked sulfated galactans with an average molar mass comprised between 7 and 1100 kDa.

Even more preferentially the cosmetic or dermocosmetic agent consists of:
 galactomannans with an average molar mass comprised between 8 and 80 kDa, and cross-linked sulfated galactans with an average molar mass comprised between 8 and 200 kDa.

Galactomannans can be obtained in particular from the hydrolysis of galactomannans native to Tara (*Caesalpinia spinosa*), guar (*Cyamopsis tetragonoloba*), carob (*Ceratonia siliqua*), but also senna (*Cassia angustifolia*), cassia (*Cassia fistula*), cassia (*Cassia obtusifolia* or *Cassia* tora), Chinese locust bean (*Gleditsia sinensis*), locust bean (*Gieditsia triacanthos*), sophora (*Sophora japonica*) and/or fenugreek (*Trigonella foenum-graecum*), preferably *Caesalpinia spinosa*.

Cross-linked sulfated galactans can be obtained by hydrolysis of sulfated galactans native to carrageenans (*Kappaphycus alvarezii, Kappaphycus striatum, Eucheuma cottonii, Eucheuma spinosum, Chondrus crispus, Gigartina skottsbergii, Sacrothalia crsipata*), or *Fucellaria fastigiata*, agar (*Gelidium sesquipedale*) or algae (*Polysiphonia lanosa* or *Codium fragile*), preferably *Kappaphycus alvarezii*.

According to a particular embodiment of the invention, the cosmetic agent consists of galactomannans obtained by hydrolysis of galactomannans native to Tara (*Caesalpinia spinosa*), guar (*Cyamopsis tetragonoloba*), carob (*Ceratonia siliqua*), but also *senna* (*Cassia angustifolia*), *cassia* (*Cassia fistula*), *cassia* (*Cassia obtusifolia* or *Cassia* tora), Chinese locust bean (*Gleditsia sinensis*), locust bean (*Gieditsia triacanthos*), *sophora* (*Sophora japonica*) and/or fenugreek (*Trigonella foenum-graecum*), preferably *Caesalpinia spinosa*; and cross-linked sulfated galactans obtained by hydrolysis of sulfated galactans native to carrageenans (*Kappaphycus alvarezii, Kappaphycus striatum, Eucheuma cottonii, Eucheuma spinosum, Chondrus crispus, Gigartina skottsbergii, Sacrothalia crsipata*), or *Fucellaria fastigiata*, agar (*Gelidium sesquipedale*) or algae (*Polysiphonia lanosa* or *Codium fragile*), preferably *Kappaphycus alvarezii*.

The galactomannans and cross-linked sulfated galactans are obtained according to the following steps:

Solubilization of native galactomannan powder or respectively native sulfated galactans in water, Hydrolysis by chemical or enzymatic route;

Separation of the soluble or insoluble phases, in order to eliminate the insoluble phase;

Selection by membrane filtration(s) of galactomannans of defined molecular weight.

The cross-linked sulfated galactans are also cross-linked by a cross-linking agent, preferentially a cross-linking agent of ionic nature.

The galactomannans and cross-linked sulfated galactans thus obtained are mixed to form a cosmetic agent.

According to a particular and preferred embodiment, the cosmetic agent a) according to the invention consists of 60 to 90% galactomannans and 10 to 40% cross-linked sulfated galactans.

According to a particular and preferred embodiment, the cosmetic agent consists of galactomannans obtained from *Caesalpinia spinosa* with molar masses comprised between 1 and 150 kDa, and of cross-linked sulfated galactans obtained from *Kappaphycus alvarezii* with molar masses comprised between 1 and 150 kDa in particular.

According to a particular embodiment of the invention, the cosmetic agent a) is present in the composition in a content ranging from 0.01% to 2% by weight of active ingredient relative to the total weight of the composition, preferentially from 0.1% to 1%, and even more preferentially from 0.4% to 0.8% by weight of active ingredient relative to the total weight of the composition.

'Active ingredient' means the active compounds of the cosmetic agent to which efficacy is attributed. It is also referred to as dry matter for plant extracts.

Such biopolymers are described in patent applications WO2017/19792 and WO2017/129780 of the Société Industrielle Limousine d'Application Biologique, in particular example 1 of application WO2017/129780. The use of these biopolymers improves the skin barrier effect by protecting the skin against the penetration of toxic molecules, such as pollutants, allergens and heavy metals. The film effect after application to the skin also improves the overall appearance of the face and helps the pigments and make-up wear.

According to a particular and preferred embodiment, a product marketed by the company SILAB under the trade name FILMEXEL® will be used as cosmetic agent consisting of galactomannans and cross-linked sulfated galactans, INCI name 'CAESALPINIA SPINOSA EXTRACT and KAPPAPHYCUS ALVAREZII EXTRACT and WATER', in powder form and composition CAESALPINIA SPINOSA EXTRACT 76%, KAPPAPHYCUS ALVAREZII EXTRACT 19%, and WATER 5% (95% active ingredient or dry matter).

*Theobroma cacao* L Hydrolysate

The *Theobroma cacao* L. hydrolysate according to the invention is a peptide and saccharide *Theobroma cacao* L bean hydrolysate comprising mainly peptides and saccharides. The term "predominantly peptides and saccharides" means an amount greater than 50%, preferentially greater than 60%, preferentially greater than 70% and up to about 90% (weight/weight) of dry matter in peptides and saccharides, preferentially 90% of the weight of the dry matter.

"Peptide and saccharide hydrolysate" means a hydrolysate comprising predominantly or essentially peptides and saccharides (mono and oligosaccharides). The proteins and polysaccharides naturally present in the beans have been hydrolyzed to peptides, oligosaccharides and monosaccharides, advantageously the hydrolysis is an enzymatic hydrolysis.

This hydrolysate can be obtained as follows:
a) ground *Theobroma cacao* L beans are dispersed in an aqueous phase;
b) an enzymatic treatment of the aqueous dispersion obtained in step a) is carried out;
c) recovery of the enzymatic hydrolysate is carried out by solid/liquid separation,
d) the hydrolysate is purified by ultra- and nanofiltration, and then optionally; e) lyophilization of the hydrolysate obtained in step d) is carried out.

The hydrolysate used according to the invention is obtained from *Theobroma cacao* L beans, as starting material, which may comprise either the bean alone or the bean and its shell, preferentially the beans comprising the bean and its shell will be used.

The non-freeze-dried cocoa hydrolysate used according to the invention comprises from 20 to 70% peptides and from 5 to 40% saccharides. The freeze-dried cocoa hydrolysate without drying support according to the invention comprises more than 90 percent dry matter comprising from 20 to 70% peptides and from 5 to 40% saccharides.

In another highly preferred embodiment according to the invention, the peptides and saccharides present in the hydrolysate used according to the invention have a molecular weight comprised between 200 Da and 10 kDa.

Thus, according to a particular and preferred embodiment, the *Theobroma cacao* L bean hydrolysate is a *Theobroma cacao* L bean peptide and saccharide hydrolysate, comprising in particular peptides and saccharides having a molecular weight comprised between 200 Da and kDa.

The resulting hydrolysate can then be further diluted with water or any solvent mixture containing water. Thus, the cocoa hydrolysate according to the invention can advantageously be diluted in one or more physiologically acceptable solvents, such as water, glycerol, ethanol, propanediol, butylene glycol, dipropylene glycol, ethoxylated or propoxylated diglycols, cyclic polyols or any mixture of these solvents.

To prepare the composition, the cocoa hydrolysate according to the invention may be in liquid or lyophilized form. According to a particular embodiment, it is in liquid form.

According to a particular and preferred embodiment, the *Theobroma cacao* L. hydrolysate used will be a product marketed by the company ASHLAN under the trade name BLUMILIGHT™) with the INCI name 'BUTYLENE GLYCOL and WATER and *THEOBROMA CACAO* (COCOA) SEED EXTRACT', in the form of a liquid and with the composition BUTYLENE GLYCOL 55%, WATER 43.75%, THEOBROMA CACAO (COCOA) SEED EXTRACT 1.25% (1.25% active ingredient or dry matter).

According to a particular embodiment, the *Theobroma cacao* L. bean hydrolysate is present in the composition in a content ranging from 0.0005 to 0.025% by weight of active ingredient relative to the total weight of the composition, preferentially from 0.001 to 0.01% by weight of active ingredient relative to the total weight of the composition.

According to a particular embodiment of the invention, the cosmetic composition further comprises a prebiotic and a probiotic. The term synbiotic or prebiotic/probiotic complex is also used to define the combination of a prebiotic and a probiotic.

Prebiotic/Probiotic Complex (Synbiotic)

"Prebiotic" refers to non-living food constituents that have the property of modulating the growth and activity of probiotic strains (lactobacilli, bifidobacteria, etc.) and other bacterial strains of the intestine that are beneficial to human health. Prebiotics are generally monosaccharides, disaccharides or oligosaccharides, which can be found naturally in fruits, vegetables, and honey and are extractable. Others are produced industrially by hydrolysis of polysaccharides (for example oligofructoses or fructo-oligosaccharides, abbreviated FOS) or synthesized by subjecting disaccharides such as lactose to the action of enzymes such as lactases with transfer activities to produce trans-galacto-oligosaccharides (TOS) or by a chemical isomerization reaction to produce lactulose. Currently, trans-galactooligosaccharides (GOS) and inulin-type fructans are those with recognized prebiotic effects.

"Probiotic or derivative" means living or inactivated microorganisms that, when ingested in sufficient amounts, exert positive health effects beyond traditional nutritional effects.

Probiotics can be either bacteria or yeast.

The probiotic or derivative may be selected from a strain of one or more of the following: *Lactobacillus*, strains and derivatives of Clostridia, strains and derivatives of *Bifidobacterium*, strains and derivatives of *Saccharomyces*, strains and derivatives of *Lactococcus*, strains and derivatives of *Pedicoccus*, strains and derivatives of *Enterococcus*, strains and derivatives of *Escherichia*, strains and derivatives of *Alcaligenes*, strains and derivatives of *Corynebacterium*, strains and derivatives of *Bacillus*, and strains and derivatives of *Propionibacterium*.

Particular mention may be made of bacteria of the genera *Lactobacillus* and *Bifidobacterium*.

The strains identified as probiotics apply mainly to the intestinal sphere, they include *Lactobacillus acidophilus, L. casei, L. gasseri, L. paracasei,* L. *Rhamnosus* and Bifidobacteria animal, *B. breve, B. longum.*

As yeasts, particular mention may be made of *Saccharomyces cerevisiae* var. *boulardii*, which occurs naturally in lychees.

'Synbiotics' refers to combinations of probiotics and prebiotics.

According to a particular embodiment, the prebiotic is selected from the group consisting of inulin and alpha-glucan oligosaccharide.

According to a particular embodiment, the probiotic is selected from the group consisting of probiotic lysates. Preferably, the probiotic lysate is a lysate of the genus *Bacillus*.

According to a particular and preferred embodiment, the cosmetic composition of the invention comprises as a prebiotic/probiotic complex Ecoskin® marketed by the company SOLABIA, which is a mixture of alpha-glucan oligosaccharide, *Polymnia sonchifolia* root juice, maltodextrin, and *Lactobacillus* sp bacteria, with the INCI name:

ALPHA-GLUCAN OLIGOSACCHARIDE and *POLYMNIA* SONCHIFOLIA ROOT JUICE and MALTODEXTRIN and *LACTOBACILLUS*

The composition of Ecoskin® is: ALPHA-GLUCAN OLIGOSACCHARIDE 70%, *POLYMNIA* SONCHIFOLIA ROOT JUICE 19%, MALTODEXTRIN 10%, *LACTOBACILLUS* 1% (corresponding to 90% active ingredient).

It is a pre/probiotic complex, spray-dried on maltodextrin, made of: α-gluco-oligosaccharides (GOS) obtained by enzymatic synthesis from vegetable substrates (corn maltose, beet sucrose), 100% pure vegetable juices rich in β-fructooligosaccharides (FOS) obtained by cold pressing of tubers of *Polymnia sonchifolia*, and a probiotic bacterium of *Lactobacillus* (L.). *casei, L. acidophilus*), inactivated by tyndallization and freeze-dried.

The prebiotic portion comes from α-gluco-oligosaccharides (GOS) and β-fructooligosaccharides from the cold-pressed extract of *Polymnia sonchifolia* tubers; these prebiotics stimulate the skin's ecoflora.

Probiotics are inactivated *Lactobacillus* bacteria that stimulate the β-defensins involved in the skin's defense system. The strains of *Lactobacillus* bacteria (*Lactobacillus casei* and *Lactobacillus acidophilus*) that are used in Ecoskin® are previously lyophilized and tyndallized, which means that their reproductive system is inactivated by heat preventing their development in cosmetic preparations containing them.

According to a particular embodiment, the prebiotic/probiotic complex is present in the composition in a content ranging from 0.05% to 3% by weight of active ingredient relative to the total weight of the composition, preferentially from 0.1 to 1% by weight of active ingredient relative to the total weight of the composition.

Galenic

The compositions according to the invention are intended more particularly for topical application to keratin materials, in particular to the skin.

The compositions of the invention comprise a cosmetically acceptable medium, i.e. one compatible with the skin and the hair and nails. The compositions may have all cosmetic forms, and in particular be in the form of creams, oil-in-water or water-in-oil emulsions or multiple emulsions, solutions, suspensions, gels, milks, lotions, serums, sticks or powders, and adapted for application to the skin, the lips and/or the hair and nails.

According to a particular embodiment, the composition of the invention is intended for topical application to the skin, the lips or the eyes and is in the form of a care product and/or a make-up product for the skin, the lips and/or the eyes, in particular for the complexion.

We will speak indifferently of skin make-up or make-up for the complexion.

'Eye make-up' means in particular liners, or eye shadows.

According to a particular and preferred embodiment, the composition of the invention is in the form of a foundation, or a base, preferably a foundation.

According to a particular and preferred embodiment, the composition of the invention is in the form of a powder, a foundation, or a base, preferably a foundation.

The cosmetic composition of the invention is advantageously in the form of an oil-in-water emulsion, a water-in-oil emulsion, a multiple emulsion, an aqueous gel.

The composition is preferably in the form of an emulsion containing an aqueous phase and an oily phase.

The aqueous phase generally represents from 1 to 99% by weight, relative to the total weight of said composition.

The composition of the invention generally comprises, in addition to the aqueous phase, also an oily phase.

An oily phase according to the invention may comprise hydrocarbon, silicone, fluorinated or non-fluorinated oils, and mixtures thereof. These oils may be volatile or non-volatile, vegetable, mineral or synthetic.

Advantageously, hydrocarbon oils will be used.

Volatile hydrocarbon oils include branched C8-C16 alkanes, branched C8-C16 esters and mixtures thereof.

Examples of non-volatile hydrocarbon oils include hydrocarbon oils, hydrocarbon oils of vegetable origin, C10-C40 synthetic ethers, C10-C40 synthetic esters, C12-C26 fatty alcohols, C12-C22 higher fatty acids, and mixtures thereof.

The oils may be present in the composition of the invention in a content ranging from 1 to 95% by weight relative to the total weight of the composition.

The composition of the invention may also include any additive commonly used in cosmetics such as UV filters, antioxidants, surfactants, gelling agents, fillers, coloring materials, preservatives, film-forming polymers, perfumes, cosmetic active agents such as emollients, moisturizers, vitamins, anti-aging agents, lightening agents, and mixtures thereof.

According to a particular embodiment of the invention, the cosmetic composition comprises at least one or more coloring materials.

The coloring materials may be selected from water-soluble or water-insoluble, fat-soluble or fat-free, organic or inorganic coloring materials optical effect materials, and mixtures thereof. For the purposes of the present invention, a coloring material is defined as a compound capable of producing a colored optical effect when formulated in sufficient amount in an appropriate cosmetic medium.

According to a particular embodiment, the one or more coloring materials are selected in particular from mineral and/or organic pigments, composite pigments (based on mineral and/or organic materials), colorants, nacres or pearlescent pigments, and mixtures thereof.

Pigments are defined as white or colored inorganic (mineral) or organic particles, insoluble in the liquid organic phase, intended to color and/or opacify the composition and/or the deposit made with the composition.

Examples of mineral pigments include titanium dioxide (rutile or anatase), optionally surface-treated; black, yellow, red and brown iron oxides; manganese violet; ultramarine blue chromium oxide hydrated chromium oxide and ferric blue.

Examples of compositions for the lips are titanium dioxide, black, yellow, red and brown iron oxides and manganese violet.

Organic pigments include, for example, D&C Red No. 19; D&C Red No. 9; D&C Red No. 22; D&C Red No. 21; D&C Red No. 28; D&C Yellow No. 6; D&C Orange No. 4; D&C Orange No. 5; D&C Red No. 27; D&C Red No. 13; D&C Red No. 7; D&C Red No. 6; D&C Yellow No. 5; D&C Red No. 36; D&C Red No. 33; D&C Orange No. 10; D&C Yellow No. 6; D&C Red No. 30; D&C Red No. 3; D&C Blue 1; carbon black and cochineal carmine lacquers.

Examples of water-soluble colorants include Yellow 5, Yellow 6, Blue 1, Green 5, Green 3, Green 6, Orange 4, Red 4, Red 21, Red 22, Red 27, Red 28, Red 33, Red 40, cochineal carmine (Cl 15850, Cl 75470).

Examples of fat-soluble colorants include Sudan Red, D&C Red 17, D&C Green 6, beta-carotene, soybean oil, Sudan Brown, D&C Yellow 11, D&C Violet 2, D&C Orange 5, quinoline yellow, annatto.

Nacres or pearlescent pigments may be selected in particular from white pearlescent pigments, such as titanium oxide-coated mica, bismuth oxychloride; and colored pearlescent pigments, such as titanium mica with iron oxides, titanium mica with ferric blue or chromium oxide, titanium mica with an organic pigment of the abovementioned type, as well as pigments based on bismuth oxychloride. Examples are the commercially available mother-of-pearl ranges Reflecks®, Ronastar®, Timiron® and Syncristal®.

In particular, the one or more coloring materials are present in the composition in a content ranging from 2% to 30% by weight, preferably from 4% to 15% by weight relative to the total weight of the composition.

According to a particular embodiment, the composition of the invention comprises pigments, in particular mineral pigments in a content ranging from 5 to 25%, in particular from 10 to 20% by weight relative to the total weight of the composition.

The fillers are selected in particular from silicas, micas, of natural or synthetic origin, kaolin, zinc and titanium oxides; calcium carbonate, magnesium carbonate and hydrocarbonate; zinc, magnesium or lithium stearate, zinc laurate, magnesium myristate; powders of synthetic polymers, such as polyethylene, polyesters, polyamides (for example nylon); powders of polyacrylic or polymethacrylic acid, silicone resin powders; mineral powders such as spherical silica; spherical titanium dioxides; glass and ceramic beads; powders of organic materials of natural origin such as corn, wheat or rice starches, cross-linked or not, and mixtures thereof.

According to a particular embodiment, the composition of the invention comprises pigments, in particular mineral pigments in a content ranging from 5 to 25%, in particular from 10 to 20% by weight relative to the total weight of the composition.

According to a particular embodiment of the invention, the cosmetic composition does not contain any cosmetic active ingredients other than those forming the subject matter of the invention.

According to another particular embodiment of the invention, the composition also contains other cosmetic and/or dermatological active ingredients. These include actives aimed at stimulating the biodiversity and/or homeostasis of the skin microbiota, cell renewal, regeneration or revitalization of the complexion (radiance), reduction of sebum production, protection against external aggressions.

Particular mention may be made of the following active ingredients aimed at stimulating:
the biodiversity and homeostasis of the skin's microbiota,
as does the active ingredient Actibiome© (Water and seawater and glycerin and *Laminaria digitata* extract and *Chlorella vulgaris* extract and saccharide isomerate and phenoxyethanol and ethylhexylglycerin), by rebalancing the skin's pH, previously reduced by a period of stress;
cell renewal, with the help of active ingredients with a "peeling" effect, alone or in combination and at an acidic pH:
by chemical means, such as Alpha Hydroxy Acids AHA (glycolic acid, lactic acid, citric acid . . . ), Beta Hydroxy Acids BHA (salicylic acid), Poly Hydroxy Acids PHA (gluconolactone);

by biological means, such as Exfolactive C EL PX© (Opuntia coccinellifera), DERMOCH DP© (*Chlorella vulgaris*), ALGOWHITE© (Ascophyllum nodosum)

by enzymatic route, such as MELACLEAR© (Gluconic acid, Sutilains);

the regeneration or revitalization of the complexion (radiance), using active ingredients:

smoothers like Retinol (vitamin A-like)

lighteners by action on melanogenesis (vitamin C derivative)

energizers such as nutrients and/or antioxidants vitamins C and E such as SEPIVITAL© (potassium ascorbyl tocopheryl phosphate)

the reduction of sebum production, using sebum-trapping agents (Clays) or sebo-regulating active agents such as Zinc gluconate (Mineralis GU/Zn) and avocado lipophyl extract (5 alpha avocuta), protection against external insult: pollution, blue light, UV using chemical or mineral filters and/or diffusing reflective particles, and mixtures thereof.

The invention also relates to a cosmetic process for the care and/or make-up of keratin materials, in particular the skin, the lips and/or the eyes, comprising at least the application to said keratin materials, in particular the skin of the face, of a composition according to the invention.

According to a particular embodiment, it is a make-up composition for the skin, the lips or the eyes, preferably for the complexion.

According to a particular embodiment, it is a skin care and/or make-up process, in particular for the skin of the face and/or neck.

According to a particular embodiment, it is a lip care and/or make-up process.

According to another particular embodiment, it is an eye care and/or make-up procedure, in particular for the eyelids.

According to a particular embodiment, the process is intended to maintain the skin ecosystem and/or maintain the balance of the skin microbiota, in particular the microbial diversity, strengthen the skin barrier and its hydrolipidic film, improve the integrity and resistance of the skin to stress, in particular preventing and/or limiting the cutaneous consequences of a hypoxic environment, promoting desquamation and/or epidermal renewal, reducing loss of firmness, reducing relaxation of pores, reducing surface irregularities, improving the homogeneity of the complexion, and/or promoting and/or improving the wear of make-up and the homogeneity of the deposit.

Another subject matter of the invention is the non-therapeutic cosmetic use of at least one cosmetic agent consisting of galactomannans with molar masses comprised between 5 and 630 kDa and cross-linked sulfated galactans with molar masses comprised between 7 and 3000 kDa, and of at least one *Theobroma cacao* L. bean hydrolysate as defined above, as a combination for maintaining the skin ecosystem and/or maintaining the balance of the skin microbiota, in particular the microbial diversity, strengthening the skin barrier and its hydrolipidic film, improving the integrity and the resistance of the skin to stress, in particular preventing and/or limiting the cutaneous consequences of a hypoxic environment, promoting desquamation and/or epidermal renewal, reducing loss of firmness, reducing relaxation of pores, reducing surface irregularities, improving the homogeneity of the complexion, promoting and/or improving the wear of make-up and the homogeneity of the deposit.

The invention also relates to at least one cosmetic agent consisting of galactomannans with molar masses comprised between 5 and 630 kDa and cross-linked sulfated galactans with molar masses comprised between 7 and 3000 kDa, and of at least one *Theobroma cacao* L. bean hydrolysate as defined above or of a composition containing them, for use in treating and/or reducing disorders associated with hyperseborrhea, in particular sebum-dependent inflammation and/or bacterial proliferation, in particular in subjects with oily skin or skin with an oily tendency.

The invention will be illustrated by the following non-limiting examples. Percentages are expressed as a percentage by weight relative to the total weight of the composition unless otherwise indicated.

EXAMPLES

Example 1: Effect of the Combination of a *Caesalpinia spinosa* Extract and a *Kappaphycus alvarezii* Extract (FILMEXEL®) in Combination with *Theobroma cacao* L Bean Hydrolysate (Blumilight™) on Keratinocytes A study on the transcriptional effects of these assets, used alone or in combination, was conducted using TaqMan Low Density Array (TLDA) technology. Thanks to this technology, the modulation of the expression of genes coding for specific proteins is studied in response to a treatment of Normal Human Keratinocytes, allowing a mapping of the gene expression of the active ingredients alone or in combination.

This approach makes it possible, in particular, to highlight the beneficial effects of the active ingredients or their combination in the areas covered by the profile: epidermis formation and desquamation, extracellular matrix, detoxification and anti-oxidation, inflammation and innate immunity.

Materials and Methods

Cells used: Normal human epidermal keratinocytes.
Culture medium: EpiLife® supplemented with HKGS (Human-Keratinocyte-Growth-Supplement)
Cutaneous origin of the cells: abdominal sampling, woman, 47 years old.
Study model: TaqMan Low Density Array (TLDA) Technology
Treatment of the cells with the compounds: 24 h
Compounds tested:
BLUMILIGHT™ (BUTYLENE GLYCOL and WATER and *THEOBROMA CACAO* (COCOA) SEED EXTRACT) at 0.05%.
FILMEXEL® (*CAESALPINIA SPINOSA* EXTRACT and *KAPPAPHYCUS ALVAREZII* EXTRACT and WATER) at 0.25%.
BLUMILIGHT™ at 0.05%+ FILMEXEL® at 0.25%.
Results
Table 1 below shows the variations in activity for the genes studied.
The experimental conditions selected are as follows:
Each test is carried out in triplicate (3 untreated and 3 treated under the same conditions);
The Fischer F-test is first applied by comparing the two data matrices. When the value is greater than α=0.05 then the variance of Student's t-test is 2, when Fischer's F-test is less than α=0.05 then the variance will be 3.
The transcriptional variations retained (significant) will be those corresponding to a Student's t-test less than or equal to α (or p)=0.05. Inhibitions are shown in light gray and stimulations in dark gray (see below), with a white background indicating non-significant variations, i.e. those corresponding to a Student's t-test greater than alpha (or p)=0.05.

The indication "ND" for "not determined" means that the gene has too little transcriptional activity to be quantified by the TLDA methodology used.

TABLE 1

| Function(s) of the gene | Gene | Symbol | Blumilight ™ 0.05% | Filmexcel ® 0.25% | Filmexcel ® 0.25% + Blumilight ™ 0.05% |
|---|---|---|---|---|---|
| Inhibition of proteases (integrity of the epidermis and its barrier) | Serpin peptidase inhibitor, Clade A, Member 3 | SERPINA3 | 0.809 | ND | 1.918 |
| Inhibition of proteases (integrity of the epidermis and its barrier) | Serpin peptidase inhibitor, Clade B, Member 3 | SERPINB3 | 1.826 | 2.562 | 3.019 |
| Formation of corneodesmosomes (intercellular cohesion and mechanical strength) | Desmoglein 1 | DSG1 | 0.971 | 2.620 | 2.997 |
| Formation of tight junctions (quality of the epidermal barrier) | Claudin-1 | CLDN1 | 1.356 | 1.705 | 2.192 |
| Control of epidermal differentiation (skin surface formation) | Krueppel-like factor 10 | KLF10 | 1.116 | 1.218 | 1.108 |
| Inflammatory and immune reaction (inflammation) | CD74 molecule, major histocompatibility complex, class II invariant chain | CD74 | 1.12 | 0.743 | 0.649 |
| Ion channel inducing apoptosis, inflammatory response and perception of irritation (inflammation, skin fragility and discomfort) | Transient receptor potential cation channel, subfamily V member 3 | TRPV3 | 0.740 | 1.134 | 0.537 |
| Wound healing and antimicrobial cytokine, (tissue repair and microbiota control) | Pro-platelet basic protein chemokine ligand 7 or CXCL7 | PPBP | 0.974 | N%D | 2.821 |

These data show, for the combinations tested, a synergistic effect with an overall effect making it possible overall to strengthen and preserve the structures of the epidermis, in particular:

to promote the integrity of the protein structures of the skin involved in its maintenance, in the astringent effect on the pores and the filling of skin reliefs, by preventing the degradation of these protein structures through the activation of the genes of protease inhibitors such as SERPINA3, SERPINB3, to reinforce the mechanical resistance of the epidermis by stimulating the transcriptional activity of the DSG1 gene involved in the formation of corneodesmosomes, (protein structure linking cells together), to improve the performance of the skin barrier by stimulating the transcriptional activity of the CLDN1 gene involved in the formation of intercellular tight junctions that limit intercellular water passage (insensible water loss) and maintain epidermal lipids on the skin surface, to promote the proper development of the epidermis in particular by stimulating the transcriptional activity of the KLF10 gene involved in the differentiation of epidermal keratinocytes and by stimulating that of the PPBP gene (alias CXCL7) involved in wound healing and vascularization, to modulate the sensory component of the epidermis in particular to weight the sensation of discomfort due to inflammation by inhibiting the transcriptional activity of the TRPV3 gene, which is also involved in the fragility of the epidermis (cell apoptosis), to increase skin control of the microbiota by stimulating the transcriptional activity of the CXCL7 gene, a bactericidal and antifungal antimicrobial cytokine.

The combination according to the invention of an extract of *Caesalpinia spinosa* and an extract of *Kappaphycus alvarezii* (Filmexel®) with *Theobroma cacao* L bean hydrolysate (Blumilight™) thus makes it possible to maintain the skin ecosystem and/or maintain the balance of the skin microbiota, in particular the microbial diversity, strengthen the skin barrier and its hydrolipidic film, improve the integrity and resistance of the skin, limit the cutaneous and sensory consequences of a hypoxic or inflammatory environment, reduce the loss of firmness, reduce the relaxation of pores and the formation of skin relief imperfections (wrinkles and fine lines), promote and/or improve the homogeneity of distribution of a make-up product.

Example 3: Cosmetic Formulations

Cosmetic formulations are prepared according to classical formulation methods.

The percentages are expressed as percentages by weight of ingredient (raw material) relative to the total weight of the composition.

A Moisturizing Day Cream for Combination to Oily Skin:

| | |
|---|---|
| VEGETABLE GLYCEROL | 6.0% |
| (Glycerin) | |
| BLUMILIGHT ™ | 0.10% |
| (Butylene glycol and Water and *Theobroma cacao* (cocoa) seed extract) | |
| FILMEXEL ® | 0.50% |
| (*Caesalpinia spinosa* fruit extract and *Kappaphycus alvarezii* extract and water) | |
| VITACTYL CLEAR 2 MB | 3.0% |
| (*Malva sylvestrys* (Mallow) extract and phenoxyethanol and water | |
| RENOHYAL | 0.10% |
| (Sodium Hyaluronate) | |
| Isononyl isononanoate | 10.0% |
| Steareth-2 | 12.5% |
| Glyceryl stearate | 1.1% |
| Stearyl alcohol | 5.0% |
| Butylene glycol | 3.0% |
| Glycerin | 2.0% |
| Curator | 0.5% |
| Water, q.s. | 100% |

A Gel for Combination Skin:

| | |
|---|---|
| VEGETABLE GLYCEROL | 6.0% |
| (Glycerin) | |
| BLUMILIGHT ™ | 0.50% |
| (Butylene glycol and Water and *Theobroma cacao* (cocoa) seed extract) | |
| FILMEXEL ® | 1.00% |
| (*Caesalpinia spinosa* fruit extract and *Kappaphycus alvarezii* extract and water) | |
| RENOHYAL | 0.1% |
| (Sodium Hyaluronate) | |
| Glycol | 3.0% |
| AMPS Polymer | 3.0% |
| Mineral oil | 2.0% |
| Polyethylene glycol | 1.5% |
| Preservative | 0.5% |
| Fragrance concentrate | 0.3% |
| Water, q.s. | 100% |

An SPF Foundation

| | |
|---|---|
| BLUMILIGHT ™ | 0.10% |
| (Butylene glycol and Water and *Theobroma cacao* (cocoa) seed extract) | |
| FILMEXEL ® | 0.50% |
| (*Caesalpinia spinosa* fruit extract and *Kappaphycus alvarezii* extract and water) | |
| UV-TITANIUM M160 | 2.0% |
| (Titanium dioxide, TiO$_2$ (nano)) | |
| ZINC OXIDE | 3.0% |
| (Zinc oxide, CI 77947) | |
| IRON OXIDES AND TITANIUM DIOXIDE | 18.0% |
| (Black CI 77499, Red CI 77491, Yellow CI 77492, White CI 77891) | |
| Cyclopentasiloxane and cyclohexasiloxane | 5.0% |
| Cetyl dimethicone | 1.0% |
| Caprylic/capric triglycerides | 2.2% |
| Octyl stearate | 1.4% |
| Mineral oil | 3.5% |
| Beeswax | 0.8% |

-continued

| | |
|---|---|
| Polymethyl methacrylate | 1.1% |
| Fragrance concentrate | 0.1% |
| Water, q.s. | 100% |

Sebum-Regulating Mask

| | |
|---|---|
| VEGETABLE GLYCEROL | 6.0% |
| (Glycerin) | |
| BLUMILIGHT ™ | 1.00% |
| (Butylene glycol and Water and *Theobroma cacao* (cocoa) seed extract) | |
| FILMEXEL ® | 0.50% |
| (*Caesalpinia spinosa* fruit extract and *Kappaphycus alvarezii* extract and water) | |
| MINERALIS Gu/Zn | 0.2% |
| (Zinc Gluconate) | |
| 5 ALPHA AVOCUTA | 1.0% |
| (Butyl avocadate, propyl gallate) | |
| Glycerin | 5.0% |
| Cetearyl alcohol & cetearyl glucoside | 3.0% |
| Myristyl alcohol & myristyl glucoside | 2.0% |
| Octyldodecanol | 3.0% |
| Pentylene glycol | 1.0% |
| Cetearyl alcohol | 0.5% |
| Sodium Polyacrylate | 0.5% |
| Stearoyl glutamate of sodium | 0.3% |
| Acrylate/C10-30 alkylacrylate crosspolymer | 0.2% |
| Xanthan gum | 0.1% |
| Disodium EDTA | 0.1% |
| Perfume | 0.1% |
| Water q.s. | 100% |

An SPF Foundation

| | |
|---|---|
| BLUMILIGHT ™ | 0.10% |
| (Butylene glycol and Water and *Theobroma cacao* (cocoa) seed extract) | |
| FILMEXEL ® | 0.50% |
| (*Caesalpinia spinosa* fruit extract and *Kappaphycus alvarezii* extract and water) | |
| ECOSKIN ® | 0.50% |
| (Alpha-glucan oligosaccharide and *Polymnia sonchifolia* root juice and Maltodextrin and *Lactobacillus*) | |
| UV-TITANIUM M160 | 2.0 |
| (Titanium dioxide, TiO$_2$ (nano)) | |
| ZINC OXIDE | 3.0% |
| (Zinc oxide, CI 77947) | |
| IRON OXIDES AND TITANIUM DIOXIDE | 16.0% |
| (Black CI 77499, Red CI 77491, Yellow CI 77492, White CI 77891) | |
| Cyclopentasiloxane and cyclohexasiloxane | 5.0% |
| Cetyl dimethicone | 1.0% |
| Caprylic/capric triglycerides | 2.2% |
| Octyl stearate | 1.4% |
| Mineral oil | 3.5% |
| Beeswax | 0.8% |
| Polymethyl methacrylate | 1.1% |
| Fragrance concentrate | 0.1% |
| Water, q.s. | 100% |

The invention claimed is:

1. A cosmetic composition comprising, in a physiologically acceptable medium, at least:
    (a) a cosmetic agent consisting of galactomannans with molar masses comprised between 5 and 630 kDa, obtained by hydrolysis of native galactomannans of *Caesalpinia spinosa*, and cross-linked sulfated galactans with molar masses comprised between 7 and 3000 kDa, obtained by hydrolysis of sulfated galactans native to *Kappaphycus alvarezii*, and
    (b) a *Theobroma cacao* L bean hydrolysate.

2. The cosmetic composition as claimed in claim 1, wherein the cosmetic agent (a) consists of 60 to 90% of galactomannans and 10 to 40% of cross-linked sulfated galactans.

3. The cosmetic composition as claimed in claim 1, wherein the cosmetic agent consists of galactomannans obtained from *Caesalpinia spinosa* with molar masses comprised between 5 and 120 kDa, and of cross-linked sulfated galactans obtained from *Kappaphycus alvarezii* with molar masses between 7 and 1100 kDa.

4. The cosmetic composition as claimed in claim 1, wherein the cosmetic agent (a) is present in the composition in a content ranging from 0.01% to 2% by weight of active ingredient relative to the total weight of the composition.

5. The cosmetic composition as claimed in claim 1, wherein the *Theobroma cacao* L bean hydrolysate is a peptide and saccharide *Theobroma cacao* L bean hydrolysate.

6. The cosmetic composition according to claim 5, wherein the *Theobroma cacao* L bean hydrolysate comprises peptides and saccharides having a molecular weight between 200 Da and 10 kDa.

7. The cosmetic composition as claimed in claim 1, wherein the *Theobroma cacao* L. bean hydrolysate is present in the composition in a content ranging from 0.0005 to 0.025% by weight of active ingredient relative to the total weight of the composition.

8. The cosmetic composition as claimed in claim 1, wherein it further comprises a prebiotic and a probiotic.

9. The cosmetic composition as claimed in claim 1, wherein it is in the form of a care product and/or a make-up product for the skin, the lips, or the eyes.

* * * * *